US008350239B2

(12) United States Patent
Roof et al.

(10) Patent No.: US 8,350,239 B2
(45) Date of Patent: Jan. 8, 2013

(54) PEN SPECIFIC FOR ERASABLE MEDIA USAGE

(75) Inventors: Bryan J. Roof, Newark, NY (US); Anthony S. Condello, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 319 days.

(21) Appl. No.: 12/573,478

(22) Filed: Oct. 5, 2009

(65) Prior Publication Data

US 2011/0079735 A1 Apr. 7, 2011

(51) Int. Cl.

| | |
|---|---|
| ***A61N 5/06*** | (2006.01) |
| ***G01J 3/10*** | (2006.01) |
| ***H05G 2/00*** | (2006.01) |

(52) U.S. Cl. ............ 250/504 R; 250/492.1; 250/504 H; 430/55; 430/66; 430/132; 430/492.1; 430/286.1; 430/270.1; 430/269

(58) Field of Classification Search ............. 250/504 R, 250/492.1; 430/55, 66, 132, 492.1, 286.1, 430/270.1, 269

See application file for complete search history.

(56) References Cited

U.S. PATENT DOCUMENTS

| | | | | |
|---|---|---|---|---|
| 5,155,607 | A * | 10/1992 | Inoue et al. | 349/89 |
| 2007/0054215 | A1 * | 3/2007 | Iftime et al. | 430/270.1 |
| 2008/0311521 | A1 * | 12/2008 | Kazmaier et al. | 430/286.1 |

* cited by examiner

*Primary Examiner* — Jack Berman

*Assistant Examiner* — Meenakshi Sahu

(74) *Attorney, Agent, or Firm* — MH2 Technology Law Group LLP

(57) ABSTRACT

Exemplary embodiments provide materials and methods for a pen that can include a writing end for writing an image on an erasable medium and an erasing end for locally erasing an image from the erasable medium.

17 Claims, 6 Drawing Sheets

PEN SPECIFIC FOR ERASABLE MEDIA USAGE

DETAILED DESCRIPTION

1. Field of Use

The present teachings relate generally to pens and, more particularly, to pens for selectively imaging and erasing erasable media.

2. Background

There are several different types of conventional pens, including ballpoint, rollerball, fountain, and felt-tip, which are used for writing. The writing is achieved by applying permanent ink to a surface of, for example, paper media.

Paper media bearing permanent ink are non-reusable and are often discarded after being read. Although paper media are relatively inexpensive, the quantity of discarded paper media is enormous and its disposal raises significant cost and environmental issues.

In contrast to paper media, erasable media may be reused many times to transiently store images and/or text. For example, an erasable medium includes a photochromic material that undergoes reversible photoinduced color change to enable image-writing and image-erasing. Ultraviolet (UV) light is often used to induce image-writing and heat is often used to induce image-erasing.

Examples of erasable medium include that described in a co-pending U.S. patent application Ser. No. 12/206,136 filed Sep. 8, 2008 and entitled “Inkless Reimageable Printing Paper and Method,” which is commonly assigned with the present application to Xerox Corp., and is incorporated in its entirety herein by reference. An embodiment of the erasable medium formulation detailed in the co-pending application includes a photochromic material, for example an alkoxy modified dithienylethene. Use of this material allows for the imaging of a pattern onto the medium using patterned ultraviolet (UV) light. The UV light chemically alters the formulation to produce a visible image pattern. The image remains visible for a period of time, but is erasable on demand using one or more of heat and visible light. The chemical formulation of the erasable medium is re-imageable such that the same or a different pattern can be re-imaged.

Conventional ink pens can not be used in the context of the reusable erasable media, due in part to the composition of erasable media and further due to the permanent nature of conventional ink pens.

Thus, there is a need to overcome these and other problems of the prior art and to provide a pen, having certain attributes of a conventional ink pen, but specific to imaging and erasing of erasable media.

SUMMARY

According to various embodiments, the present teachings include a pen. The pen can include a pen barrel, a first radiant energy source mounted within a first end of the pen barrel, and a second radiant energy source mounted within a second end of the pen barrel. The first radiant energy source is configured to image an erasable medium, while the second radiant energy source is configured to erase an imaged region of the erasable medium.

According to various embodiments, the present teachings also include a method for making a pen. The pen can be made by first providing a pen barrel and then mounting a first radiant energy source within a first end of the pen barrel. The first radiant energy source can be configured to output light at a wavelength configured to image an erasable medium. A second radiant energy source can also be mounted within a second end of the pen barrel and configured to erase an imaged region of the erasable medium.

According to various embodiments, the present teachings further include a method for using a pen by first providing a pen that includes a writing end and an erasing end. The writing end of the pen can include a radiant energy source that can be activated to emit light and configured to image the erasable medium.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

It should be noted that some details of the figures have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. Wherever possible, the same reference numbers will be used throughout the drawings to refer to the same or like parts.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Exemplary embodiments provide materials and methods for pens configured for use with erasable media. Specifically, the pen can include a writing end for generating an image and/or text on an erasable medium and an erasing end for selectively or locally erasing an imaged erasable medium.

As used herein, the term “erasable medium” refers to a substrate including an imaging medium that can be reused multiple times to transiently store and/or remove images and/or text. In embodiments, the imaging medium can include a photochromic material that can undergo reversible color change to enable image-writing and image-erasing.

The substrate of the erasable medium can be, for example paper, glass, ceramic, wood, plastic, fabric, textile, and/or metal. In embodiments, the "erasable medium" can have the appearance and feel of traditional paper, including cardstock and other weights of paper.

As used herein, the term "imaged erasable medium" refers to an erasable medium bearing a visible image, the image a result of, for example, ultraviolet (UV) writing of the erasable medium.

As used herein, the term "non-imaged erasable medium" refers to an erasable medium which has not been previously imaged, or an erasable medium having an image erased therefrom and available for writing. An exemplary erasable medium is described in connection with FIG. 1 below.

Figure 1:
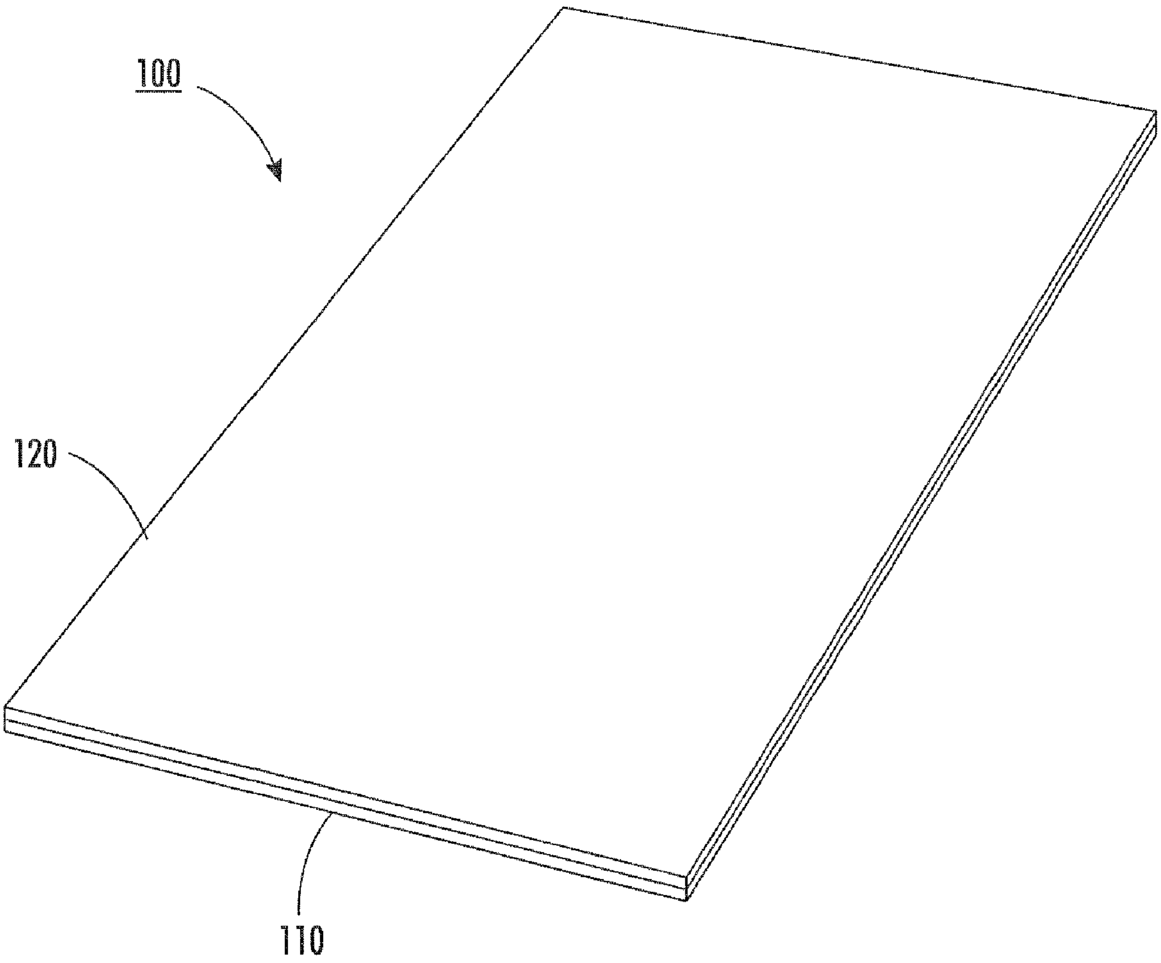
FIG. 1 is a perspective depiction of an erasable medium having a photochromic material.

FIG. 1 depicts an exemplary erasable medium 100 in accordance with the present teachings. It should be readily apparent to one of ordinary skill in the art that the erasable medium 100 depicted in FIG. 1 represents a generalized schematic illustration and that other layers or materials can be added or existing layers or materials can be removed or modified.

As shown in FIG. 1, the erasable medium 100 can include a substrate 110 and a photochromic material 120 incorporated into or onto the substrate 110. The photochromic material 120 can provide a reversible writing erasable image-forming formulation on the substrate 110.

The substrate 110 can include, for example, any suitable material such as paper, glass, ceramic, wood, plastics, fabrics, textile products, polymeric films, inorganic substrates such as metals, and the like. The paper can include, for example, plain papers such as XEROX® 4024 papers, ruled notebook paper, bond paper, and silica coated papers such as Sharp Company silica coated paper, AO paper, and the like. The substrate 110, such as a sheet of paper, can have a blank appearance.

In various embodiments, the substrate 110 can be made of a flexible material and can be transparent or opaque. The substrate 110 can be a single layer or multi-layer where each layer is the same or different material and can have a thickness, for example, ranging from about 0.05 mm to about 5 mm.

The photochromic material 120 can be impregnated, embedded or coated to the substrate 110, for example, a porous substrate such as paper. In various embodiments, the photochromic material 120 can be applied uniformly to the substrate 110 and/or fused or otherwise permanently affixed thereto.

Images formed in/on an erasable medium can be selectively or locally erased. In order to effect the transition from a visible image to an erased medium, radiant energy and/or heat can be applied to the imaged erasable medium at a temperature suitable for effecting the erasure. In embodiments, the temperature suitable for effecting the erasure can be, for example, above about 70° C., such as from about 80° C. to about 200° C. In an exemplary embodiment, the imaged erasable medium can be completely erased, for example, at about 160° C. or higher.

In embodiments, in order to image an original erasable medium or re-image the erased erasable medium, the erasable medium can be pre-heated to a temperature of about 55° C. or higher before writing, for example, using a radiant energy such as a UV exposure.

It will be appreciated that other types of erasable media, other than photochromic media, can be used in connection with the exemplary embodiments herein. Such types of erasable media are intended to be included within the scope of the disclosure.

In embodiments, the photochromic material 120 can include, for example, an inkless erasable imaging formulation as described in U.S. patent application Ser. No. 12/206,136 filed Sep. 8, 2008 and entitled "Inkless Reimageable Printing Paper and Method," which is commonly assigned with the present application to Xerox Corp., and is incorporated in its entirety herein by reference.

Disclosed herein is a pen that can be used to selectively or locally write images on erasable media. The disclosed pen can also be used to selectively or locally erase images from the erasable media such that the erased erasable media can be reused or re-imaged.

In various embodiments, the disclosed pen can include a first radiant energy source to emit radiant energy onto an erasable medium. The first radiant energy source can include, for example, UV light directed onto the photochromic material 120 of the erasable medium 100 to mark, print or write a visible image that has a color contrast with the surrounding background area of the medium 100. The disclosed pen can also include a second radiant energy source to provide light and/or heat to locally erase an imaged erasable medium.

Figure 2A:
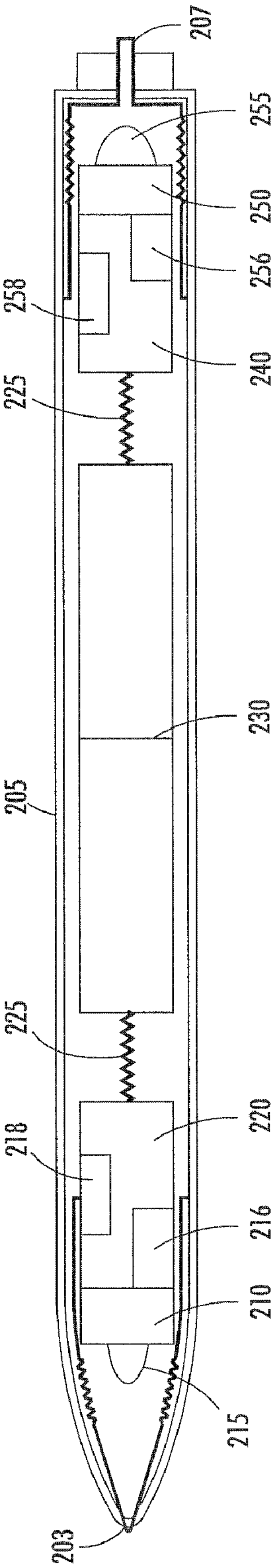
FIG. 2A depicts an exemplary pen configured for use with an erasable medium in accordance with various embodiments of the present teachings.

FIG. 2A depicts an exemplary pen 200 in accordance with various embodiments of the present teachings. It should be readily apparent to one of ordinary skill in the art that the pen 200 depicted in FIG. 2A represents a generalized schematic illustration and that other components can be added or existing components can be removed or modified.

In embodiments, the pen 200 can include a pen barrel 205 having a first end and a second end. For purposes of description, the first end can be configured for writing and the second end can be configured for erasing an imaged erasable media. The pen barrel 205 can be at least partially made of, for example, a plastic, or a metal.

In embodiments, the writing end of the pen 200 can include a first radiant energy source 215 configured within the pen barrel 205 for emitting radiant energy to write visible images on an erasable medium, such as the erasable medium 100. The imaging radiant energy can have a wavelength in a range of from about 10 nanometers to about 475 nanometers.

In embodiments, the erasing end of the pen 200 can include a second radiant energy source 255 configured within the pen barrel 205 for generating heat to locally erase an imaged erasable medium. The second radiant energy source 255 can include an IR radiation and/or light of a second wavelength (e.g. visible light). The second radiant energy source 255 can be of an intensity and duration to effect a reversible transition between a colored state and a colorless state of the erasable medium.

In various embodiments, the photochromic material 120 of the erasable medium 100 can be imaged by, for example, irradiation of a first wavelength from the first radiant energy source 215 and erased by, for example, visible light and/or heat generated by the second radiant energy source 255 as described above.

Referring back to FIG. 2A, an energy source 230 can also be configured within the pen barrel 205 and can be controllably connected to at least one of the first radiant energy source 215 and the second radiant energy source 255 such that a complete circuit can be formed to include at least one of the first radiant energy source 215 and the second radiant energy source 255.

In embodiments, the energy source 230 can be configured to separately power one of a writing and an erasing function. The energy source 230 can incorporate internal energy storage devices including, for example, one or more batteries. In embodiments, built in switches and safety devices can be incorporated to ensure which end of the pen 200 is activated for writing or for erasing. In embodiments, the energy source 230 can include recharging cradles, for example, similar to the type used for a cell phone, such that the disclosed pen 200 can be used more frequently.

As shown in FIG. 2A, the writing end including the first radiant energy source 215 can further include a writing tip 203, a first activation switch 218, and a first circuit board 220.

The first radiant energy source 215 can be mounted in a housing 210 within the writing end of the pen 200. The activation switch 218 can be incorporated with the first radiant energy source 215 and can be mounted on the associated first circuit board 220.

The writing tip 203 can move relative to the pen barrel 205 through an end opening (e.g., see 201 of FIG. 3A) of the pen barrel 205. In various exemplary embodiments, the writing tip 203 can protrude outside the pen barrel 205 at one end and can be configured to connect to the first activation switch 218 at the other end. The writing tip 203 can include an aperture formed therein, through which the first radiant energy source 215 can be output. The writing tip 203 can include a bulb or similar transparent material through which the first radiant energy source 215 can pass. In embodiments, the writing tip 203 can be a force sensitive tip connected to the first activation switch 218 in a manner such that when the writing tip 203 is pressed to a material, such as the erasable medium 100, the first activation switch 218 can be tuned on to activate the first radiant energy source 215.

In various embodiments, the first radiant energy source 215 can output, for example, UV light for writing on the erasable medium 100. The exemplary UV light can have a wavelength ranging from about 10 nm to about 450 nm at an intensity and duration sufficient to produce an image in/on the erasable medium 100, depending on the type of the photochromic material 120. In embodiments, the first radiant energy source 215 can include a UV light emitting diode (LED) or UV laser diode (LD) emitting at a wavelength to activate the photochromic formulation of the erasable medium and render an image.

In a write configuration, one end of the pen, for example, that including a negative electrode of the energy source 230, can be connected to a conductive spring 225, which can be connected to the first circuit board 220. The first circuit board 220 can further be connected to the negative end of the first radiant energy source housing 210 that may include the exemplary LED or LD. The positive end of the first radiant energy source housing 210 can be connected to the positive electrode of energy source 230 via, for example, an electrical conduction path (not shown), thereby forming a complete circuit. The electrical conduction path can include, e.g., metallic materials or conductive springs assembled within the pen barrel 205 as known to one of ordinary skill in the art.

In embodiments, pushing the writing tip 203 through the corresponding barrel aperture against the erasable medium 100 can trigger the activation switch 218 of the first radiant energy source 215. The circuitry of the first circuit board 220 in the writing end can be configured to enable the first radiant energy source 215 to emit a beam of UV light through the writing tip 203. The beam of UV light can be used to image the erasable medium 100. In operation, the pen 200 can have a feel similar to that of a normal writing implement, for example, a conventional ink pen. The writing end of the pen 200 can include a focusing lens (not shown) in order to adjust a focus the radiant energy source 215.

In embodiments, when writing on the erasable medium 100 using pen 200, the first radiant energy source 215 can be focused or collimated in order to adjust a diameter of UV light emitted from the first radiant energy source 215 at the writing tip 203. The diameter of UV light emitted can correspond to an imaged line thickness appearing on the erasable medium 100. In embodiments, the written lines generated by the writing tip 203 of the pen 200 can have a thickness or diameter of about 2 mm or less, for example, from about 0.1 mm to about 1.2 mm or from about 0.2 mm to about 1.0 mm.

Figure 2B:
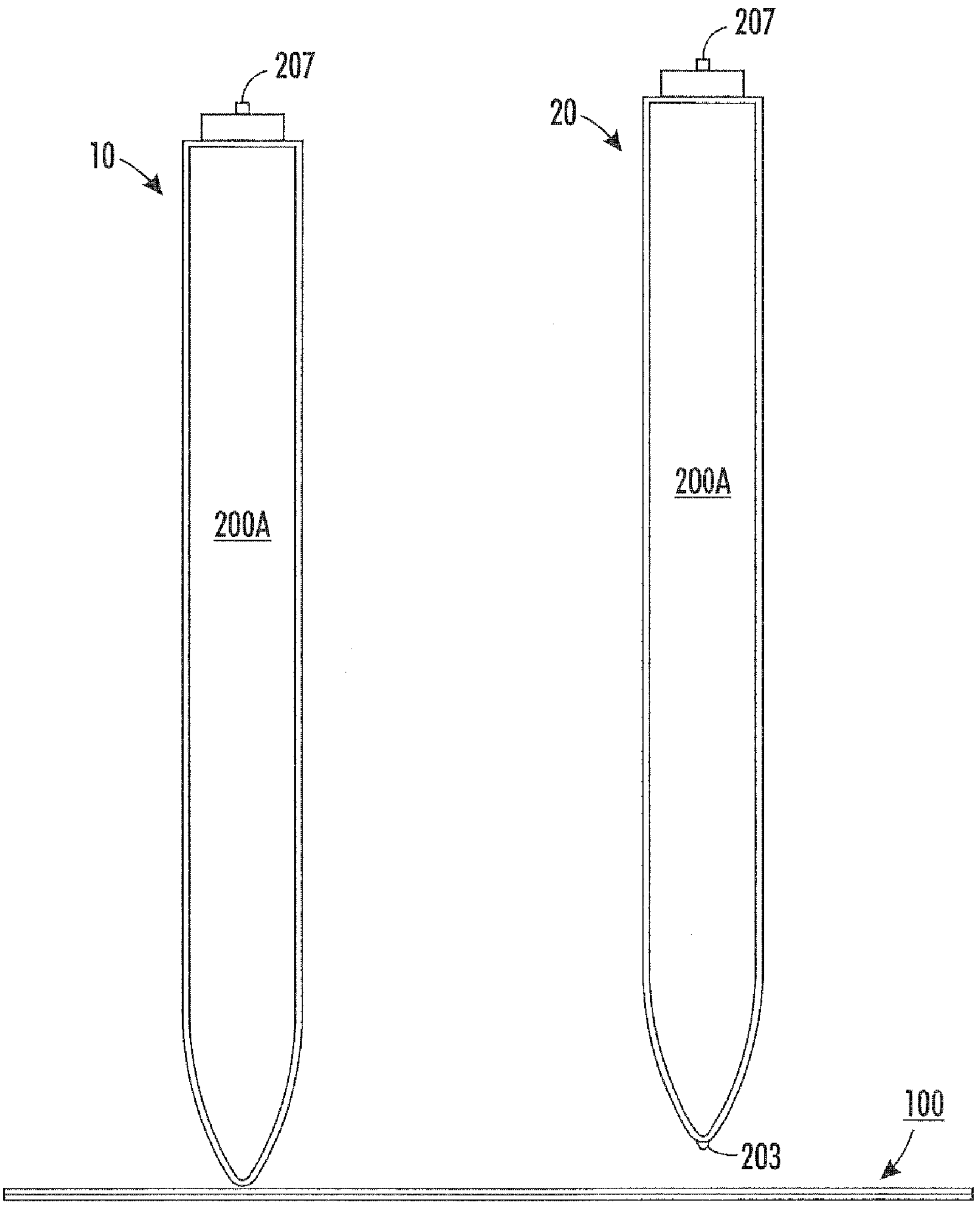
FIGS. 2B-2C depict the exemplary pen of FIG. 2A when used for writing and erasing in accordance with various embodiments of the present teachings.

In embodiments, for safety reasons, the activation switch 218 corresponding to the writing tip 203 can ensure activation of the first radiant energy source 215 only when the writing tip 203 is pressed against the erasable medium 100 as shown in FIG. 2B at 10. In embodiments, additional components can be configured to prevent the pen 200 from being turned on, if in contact with, e.g., human skin. For example, a resistance checking device 216 (see FIG. 2A) can be assembled within the writing end in connection with or on the first circuit board 220 to establish a safe resistance for writing. For example, when an undesirable resistance is measured, such as when the writing tip 203 touches human skin, the activation switch 218 can be controlled to disable the first radiant energy source 215.

Upon completion of a writing function, the pen 200 can be lifted from the erasable medium 100, as shown in FIG. 2B at 20, to release the force sensitive writing tip 203. Release of the force sensitive writing tip 203 can deactivate the first activation switch 218, and thereby turn off the first radiant energy source 215.

Figure 2C:
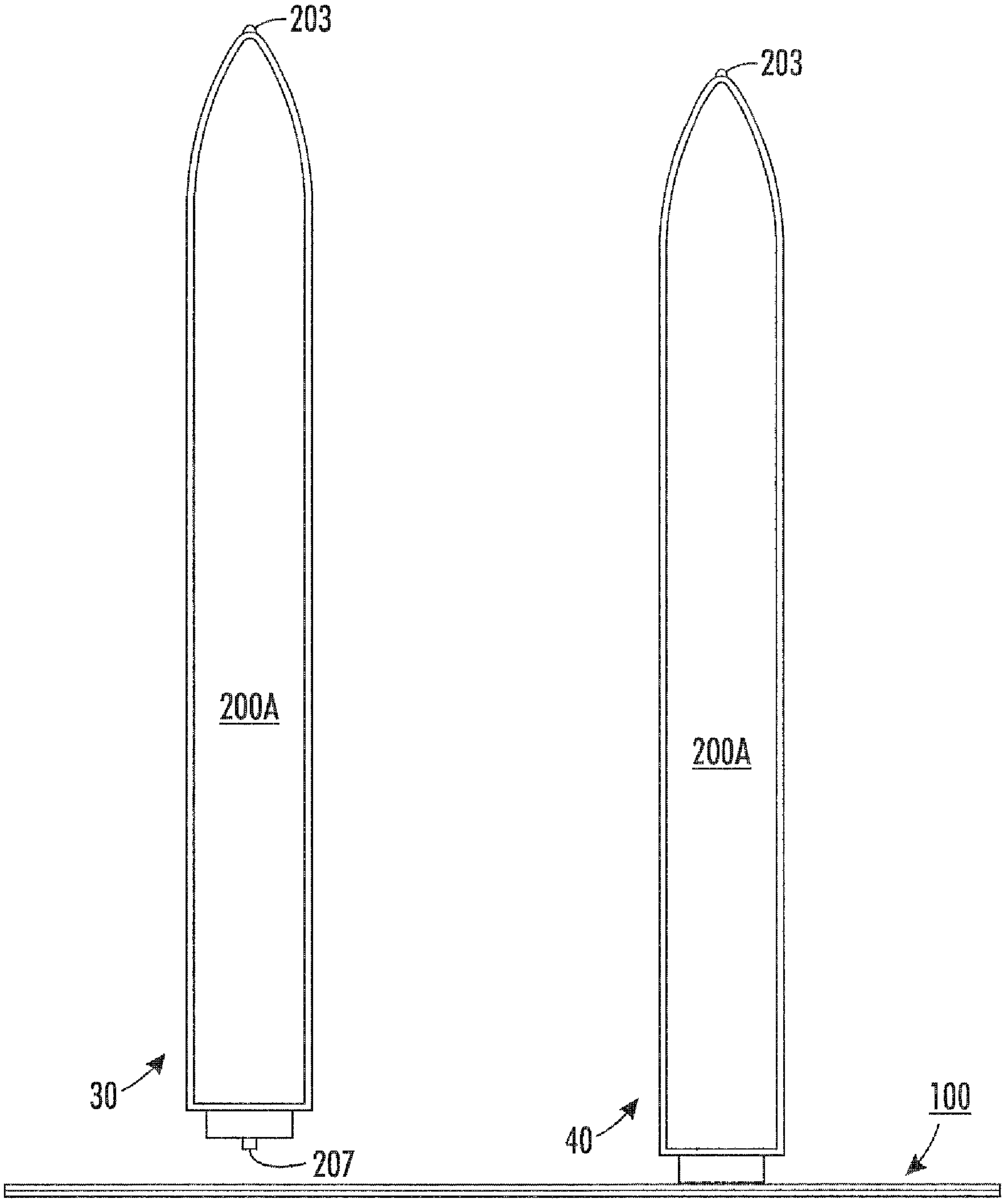

In various embodiments, when erasing is desired, e.g., if a person makes a mistake in writing or desires to revise previously printed text/images, the pen 200 can then be turned over to use the other end, i.e., the erasing end, as shown in FIG. 2C at 30.

Referring back to FIG. 2A, the erasing end of the pen 200 that includes the second radiant energy source 255 can further include a force sensitive erasing tip 207, a second activation switch 258, and a second circuit board 240, which in embodiments are configured similarly to the configuration of the writing end of the pen, except that the second radiant energy source 255 is used for erasing while the first radiant energy source 215 is used for writing.

For example, the second radiant energy source 255 can be mounted in a source housing 250 within the erasing end of the pen 200. The second activation switch 258 can be integrated with the second radiant energy source 255. The activation switch 258 can also be mounted on the associated second circuit board 240.

In embodiments, the force sensitive erasing tip 207 can be configured similar to the force sensitive writing tip 203. For example, the force sensitive erasing tip 207 can move relative to an opening (see 209 in FIG. 3B) formed in the pen barrel 205. For example, the erasing tip 207 can protrude outside the pen barrel 205 at one end (e.g., the erasing end) through the opening 209 and can be configured to connect to the second activation switch 258 at the other end. The erasing tip 207 can include an aperture formed therein, through which the second radiant energy source 255 can be output. The erasing tip 207 can include a bulb or similar transparent material through which the second radiant energy source 255 can pass.

In embodiments, the force sensitive erasing tip 207 can be configured to render the second activation switch 258 operable by pressing the force sensitive erasing tip 207 against a material, for example, the erasable medium 100. In turn, the second activation switch 258 can activate the second radiant energy source 255.

In various embodiments, the second radiant energy source 255 can be any heat-producing source, for example, a radiant heat generated by an IR irradiation and/or a visible light irradiation. In an exemplary embodiment, the second radiant energy source 255 can be activated to provide the IR radiation through a focusing lens (not shown) within the erasing tip 207, thereby locally illuminating and/or heating an imaged erasable medium to locally erase images. In embodiments, using the IR source to heat the erasable medium can expedite erasure of the heated image region from the photochromic formulation 120 of the erasable medium 100. In embodiments, the IR source can be enabled simultaneously with another light source having a second wavelength of, for example, visible light optimized for generating heat.

In embodiments, the erasing operation can use the same batteries or different batteries of the energy source 230, for example, configured with safety devices such that no UV light is emitted from the first radiant energy source 215 when the second radiant energy source 255 is activated for erasing, or vice versa.

When the second radiant energy source 255 is activated for erasing, a complete circuit can be formed by connecting the energy source 230 with the conductive spring 225 which is in turn connected to the second circuit board 240. The second circuit board 240 can also be connected to an electrode of the housing 250 whose opposite electrode is connected to the other end of energy source 230 via, for example, an electrical conduction path (not shown). The electrical conduction path can include, for example, metallic materials or conductive springs assembled within the pen barrel 205 as would be understood by one of ordinary skill in the art.

In embodiments, when the "eraser" is activated, for example, by pushing the erasing tip 207 against the erasable medium 100 as shown in FIG. 2C at 40, a narrow beam of light or heat generating light can be directed at a localized region of the imaged erasable medium, thereby locally erasing an image without erasing the entire erasable medium. Additionally, if the erasable medium substrate 110 is comprised of paper, the poor thermal conductivity of the paper can aid in erasing by retaining and transmitting heat generated by the erasing beam. In embodiments, the erasing beam generated locally on the imaged erasable medium can have a thickness or diameter of about 4 mm or less, for example, from about 0.5 mm to about 3.5 mm or from about 1.0 mm to about 3.0 mm.

In embodiments for safety reasons, the second activation switch 258 at the erasing tip 207 can ensure that the pen 200 is activated to erase only when the erasing tip 207 is pushed against the erasable medium 100. In embodiments, additional components can prevent the pen 200 from being turned on if the pen is in contact with, e.g., human skin. For example, a resistance checking device 256 can be configured within the erasing end and connected to the second circuit board 250 to determine a safe resistance for erasing. In this case, when an undesirable resistance is measured, for example, when the erasing tip 207 touches human skin, the activation switch 258 is disabled and the second radiant energy source 255 can not function.

Upon completion of an erasing function, the pen 200 can be lifted from the erasable medium 100 to release the force sensitive erasing tip 207. Release of the force sensitive erasing tip 207 can deactivate the activation switch 258 and thereby turn off the second radiant energy source 255.

In this manner, activation of the pen 200 for writing and/or erasing an image can be realized by the force sensitive tips 203/207. In various embodiments, activation capabilities for writing and/or erasing with the pen 200 can be realized by using a press button as shown in FIGS. 3A-3B.

Figure 3A:
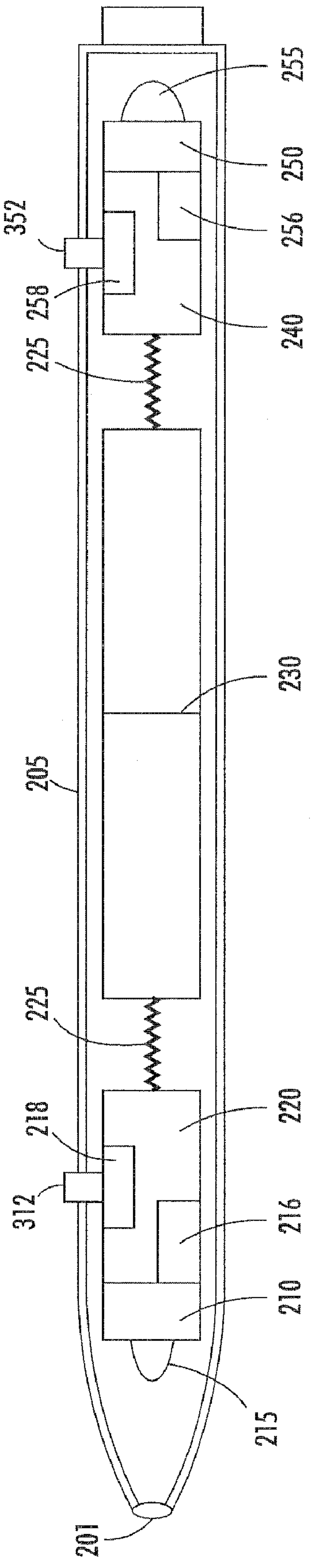
FIGS. 3A-3B depict another exemplary pen configured for use with an erasable medium in accordance with various embodiments of the present teachings.
Figure 3B:
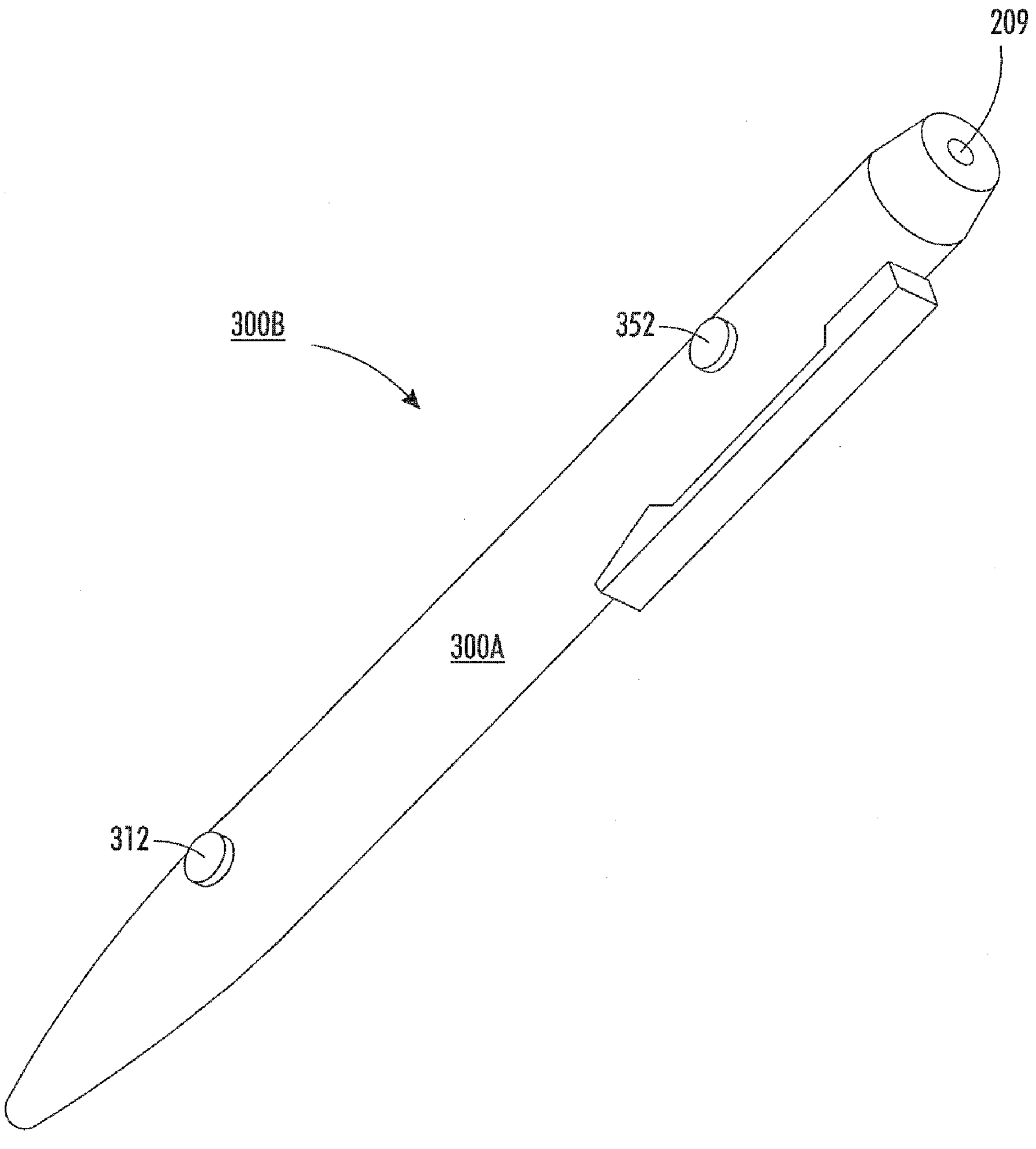

Specifically, FIGS. 3A-3B depict a second exemplary pen 300 in accordance with various embodiments of the present teachings. The pen 300 can include a press button 312 configured to control the activation switch 218 and activate the first radiant energy source 215, whereas the pen 200 uses the force sensitive writing tip 203 to control the activation switch 218. Likewise, the pen 300 can include a second press button 352 configured to control the second activation switch 258 to activate the second radiant energy source 255 instead of using the force sensitive erasing tip 207 to control the activation switch 258 in the pen 200 of FIGS. 2A-2C.

Proximate the writing end of the pen 300, the first press button 312 can, for example, slidably extend through the pen barrel 205 and detachably engage with the first activation switch 218. The first activation switch 218 can be integrated with the first radiant energy source 215 and can be mounted on the first circuit board 220. In operation, when the press button 312 is pressed to contact and activate the first activation switch 218 of the first radiant energy source 215, the circuitry of the first circuit board 220 in the writing end can be controlled so as to enable the first radiant energy source 215 to emit a beam for writing images on the erasable medium, as similarly described in FIGS. 2A-2C. Upon completion of a writing function, the press button 312 can be released or otherwise withdrawn to detach from the activation switch 218, thereby disabling the first radiant energy source 215.

In the erasing end of the pen 300, the second press button 352 can, for example, slidably extend through the pen barrel 205 and detachably engage with the second activation switch 258. The activation switch 258 can be integrated with the second radiant energy source 255 and can be mounted on the associated second circuit board 240. In operation, when the second press button 352 is pressed to contact and activate the second activation switch 258 of the second radiant energy source 255, the circuitry of the second circuit board 240 in the erasing end can be controlled to enable the second radiant energy source 255 to emit an erasing beam for locally erasing images on the erasable medium 100, as similarly described in FIGS. 2A-2C.

Upon completion of an erasing function, the second press button 352 can be released or otherwise withdrawn to detach from the second activation switch 258, thereby disabling the second radiant energy source 255.

In embodiments, instead of having a distinct writing and erasing press buttons 312 and 352, the pen 300 can have a common press button, slide switch, etc., selectively actuatable for writing or for erasing.

In embodiments, although the writing end and the erasing end of the pen barrel 205 have different pen tip configurations as shown in FIGS. 2A-2C and FIGS. 3A-3B, one of ordinary skill in the art will understand that any possible shape of the pen tip configuration can be used for the writing end and/or the erasing end.

In various embodiments, the disclosed pen, for example, as shown in FIGS. 2A-2C and FIGS. 3A-3B, can further be configured to include a conventional ink pen portion. For example, the conventional ink pen portion can have an ink head incorporated in the writing end and/or erasing end of the pen barrel 205. In this case, the disclosed pen can be used for both erasable media and conventional media for example a paper medium. In an exemplary embodiment, the ink pen head can be configured in a manner as in any known conventional pens to write with ink and in a manner to automatically retract into the pen barrel 205 when the first (or second) radiant energy source is initiated to write (or erase).

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function.

Furthermore, to the extent that the terms “including”, “includes”, “having”, “has”, “with”, or variants thereof are used in either the detailed description and the claims, such terms are intended to be inclusive in a manner similar to the term “comprising.” As used herein, the term “one or more of” with respect to a listing of items such as, for example, A and B, means A alone, B alone, or A and B. The term “at least one of” is used to mean one or more of the listed items can be selected.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of “less than 10” can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as “less than 10” can assume values as defined earlier plus negative values, e.g. −1, −1.2, −1.89, −2, −2.5, −3, −10, −20, −30, etc.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:

1. A pen comprising:

a pen barrel;

a first radiant energy source mounted within a first end of the pen barrel and configured to image an erasable medium;

a second radiant energy source mounted within a second end of the pen barrel and configured to erase an imaged region of the erasable medium;

a circuit board connected to the first radiant energy source and to an energy source;

an activation switch mounted on the circuit board; and a force sensitive writing tip connected to the activation switch, wherein pushing the force sensitive writing tip against the erasable medium activates the first radiant energy source.

2. The pen of claim 1, wherein the second radiant energy source generates heat to erase the imaged region.

3. The pen of claim 1, wherein the first radiant energy source outputs light at a wavelength configured to image the erasable medium.

4. The pen of claim 1, wherein the first radiant energy source comprises a UV light emitting diode (LED) or a UV laser diode (LD).

5. The pen of claim 1, wherein the imaged erasable medium has an image line thickness of about 2 mm or less.

6. The pen of claim 1, wherein the second radiant energy source generates an erasing beam on the imaged region having a beam thickness of about 4 mm or less.

7. The pen of claim 1, further comprising an energy source configured to power at least one of the first radiant energy source and the second radiant energy source.

8. The pen of claim 7, wherein the energy source comprises at least one of a recharging cradle and an internal device within the pen barrel that comprises at least one battery.

9. The pen of claim 1, further comprising a resistance checking device configured to determine a resistance of the pen during imaging.

10. The pen of claim 1, wherein the first end of the pen barrel further comprises:

a circuit board connected to the first radiant energy source and to an energy source, an activation switch mounted on the circuit board, and a press button detachably engaging with the activation switch to control an activation of the first radiant energy source.

11. The pen of claim 1, wherein the second end of the pen barrel further comprises:

a circuit board connected to the second radiant energy source and to an energy source, an activation switch mounted on the circuit board, and a force sensitive erasing tip connected to the activation switch, wherein pushing the force sensitive erasing tip against the erasable medium activates the second radiant energy source.

12. The pen of claim 1, further comprising a resistance checking device configured to determine a resistance of the pen during erasing.

13. The pen of claim 1, wherein the second end of the pen barrel further comprises:

a circuit board connected to the second radiant energy source and to an energy source, an activation switch mounted on the circuit board, and a press button detachably engaging with the activation switch to control an activation of the second radiant energy source.

14. A method for making a pen comprising:

providing a pen barrel;

mounting a first radiant energy source within a first end of the pen barrel, wherein the first radiant energy source is configured to output light at a wavelength configured to image an erasable medium;

mounting a second radiant energy source within a second end of the pen barrel, wherein the second radiant energy source is configured to erase an imaged region of the erasable medium;

connecting a circuit board to the first radiant energy source;

mounting an activation switch on the circuit board; and configuring at least one of a force sensitive tip and a press button in connection with the activation switch to control an activation of the first radiant energy source.

15. The method of claim 14, further comprising configuring an energy source within the pen barrel to power at least one of the first radiant energy source and the second radiant energy source.

16. The method of claim 14, further comprising:

connecting a circuit board to the second radiant energy source;

mounting an activation switch on the circuit board, and configuring at least one of a force sensitive tip and a press button in connection with the activation switch to control an activation of the second radiant energy source.

17. A method for using a pen comprising:

providing a pen comprising a writing end and an erasing end, wherein the writing end comprises a radiant energy source disposed within the pen; and activating the radiant energy source to emit light configured to image the erasable medium, wherein activating comprises pushing a force sensitive writing tip against the erasable medium; and lifting the force sensitive writing tip from the erasable medium to terminate the radiant energy source.

* * * * *